(12) United States Patent
Carlson et al.

(10) Patent No.: US 9,625,066 B2
(45) Date of Patent: Apr. 18, 2017

(54) HELICALLY WOUND PLASTIC TUBING WITH VARIABLE PROFILE THICKNESS AND METHODS OF MAKING THE SAME

(71) Applicant: Steward Plastics, Inc., Laguna Hills, CA (US)

(72) Inventors: Eric Carlson, Trabuco Canyon, CA (US); Tamsen Hughes, Trabuco Canyon, CA (US); Robert Manson, Trabuco Canyon, CA (US); Daniel Chronister, Laguna Hills, CA (US); Craig Brittain, Lake Forest, CA (US)

(73) Assignee: STEWARD PLASTICS, INC., Laguna Hills, CA (US)

(*) Notice: Subject to any disclaimer, the term of this patent is extended or adjusted under 35 U.S.C. 154(b) by 338 days.

(21) Appl. No.: 14/266,440

(22) Filed: Apr. 30, 2014

(65) Prior Publication Data

US 2015/0276097 A1    Oct. 1, 2015

Related U.S. Application Data

(60) Provisional application No. 61/971,435, filed on Mar. 27, 2014.

(51) Int. Cl.
| | |
|---|---|
| *F16L 11/24* | (2006.01) |
| *B29C 53/62* | (2006.01) |
| *A61M 39/08* | (2006.01) |
| *F16L 11/115* | (2006.01) |
| *B29L 23/00* | (2006.01) |
| *B29K 101/12* | (2006.01) |

(52) U.S. Cl.
CPC .............. *F16L 11/24* (2013.01); *A61M 39/08* (2013.01); *B29C 53/62* (2013.01); *F16L 11/115* (2013.01); *B29K 2101/12* (2013.01); *B29L 2023/005* (2013.01)

(58) Field of Classification Search
USPC .................................. 138/122, 129, 132, 133
See application file for complete search history.

(56) References Cited

U.S. PATENT DOCUMENTS

| 2,707,490 | A | * | 5/1955 | Harris | ................... B29D 23/18 |
| | | | | | 138/133 |
| 3,674,056 | A | | 7/1972 | D'Aprile | |
| 3,938,929 | A | * | 2/1976 | Stent | ..................... B29C 53/785 |
| | | | | | 264/171.29 |
| 4,204,562 | A | | 5/1980 | Kelly | |
| 4,368,088 | A | * | 1/1983 | Asakura | ................. B29C 53/586 |
| | | | | | 138/122 |
| 4,471,813 | A | * | 9/1984 | Cothran | ................... F16L 11/16 |
| | | | | | 138/122 |
| 4,490,575 | A | * | 12/1984 | Kutnyak | ................... A47L 9/24 |
| | | | | | 138/129 |
| 5,454,061 | A | | 9/1995 | Carlson | |
| 5,637,168 | A | * | 6/1997 | Carlson | ................... B29C 66/49 |
| | | | | | 156/143 |
| 5,730,188 | A | | 3/1998 | Kalman et al. | |
| 5,848,223 | A | | 12/1998 | Carlson | |

(Continued)

*Primary Examiner* — James Hook

(57) ABSTRACT

Plastic tubing including a thermoplastic ribbon helically wrapped and heat bonded to itself to form a tubing wall and a thermoplastic reinforcement located helically around and along the tubing wall. At least a thickness of the tubing wall or a size of the thermoplastic reinforcement is varied along the tubing wall.

14 Claims, 8 Drawing Sheets

(56) References Cited

U.S. PATENT DOCUMENTS

| | | | |
|---|---|---|---|
| 5,954,096 | A | 9/1999 | Lepoutre |
| 6,158,477 | A | 12/2000 | Waters |
| 6,186,183 | B1 | 2/2001 | Lepoutre |
| 6,190,480 | B1 | 2/2001 | Carlson |
| 6,367,510 | B1 * | 4/2002 | Carlson ................ A61M 16/08 138/121 |
| 6,550,501 | B2 | 4/2003 | Hupertz |
| 6,668,867 | B2 | 12/2003 | Espinasse et al. |
| 6,827,109 | B2 * | 12/2004 | McCaughtry .......... F16L 11/112 138/122 |
| 6,907,906 | B1 * | 6/2005 | Cook .................... F16L 11/115 138/109 |
| 7,965,930 | B2 | 6/2011 | Carlson et al. |
| 8,563,863 | B2 | 10/2013 | Carlson |
| 8,563,864 | B2 | 10/2013 | Carlson |
| 8,936,047 | B2 * | 1/2015 | Hahn .................... B29C 53/58 138/121 |
| 2003/0183294 | A1 * | 10/2003 | Carlson ................ A61M 16/08 138/129 |
| 2004/0081784 | A1 * | 4/2004 | Smith ................... A61M 11/08 428/36.9 |
| 2011/0168287 | A1 | 7/2011 | Carlson |
| 2014/0037276 | A1 * | 2/2014 | Carlson ............... F16L 11/1185 392/468 |

* cited by examiner

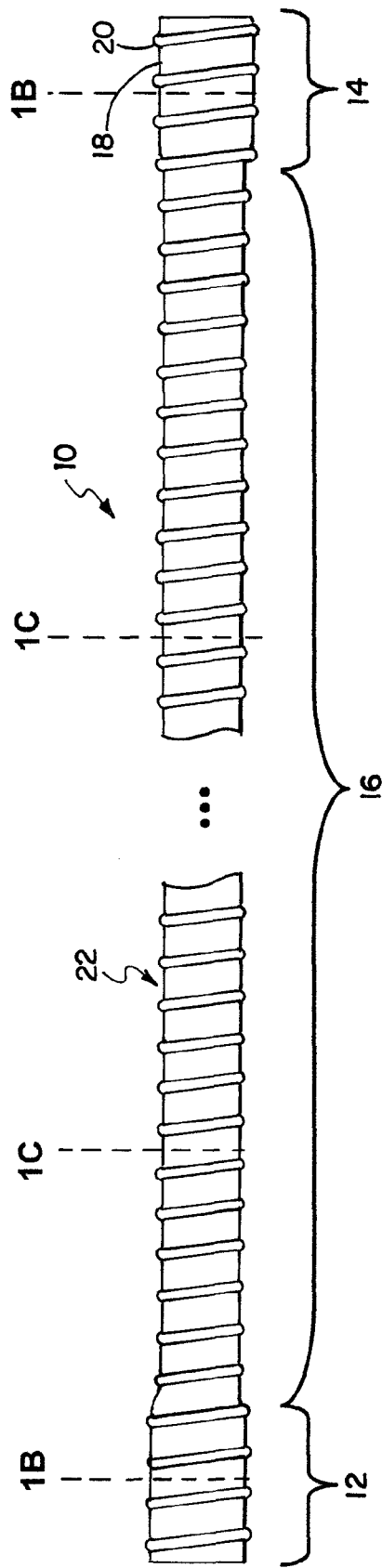

HELICALLY WOUND PLASTIC TUBING WITH VARIABLE PROFILE THICKNESS AND METHODS OF MAKING THE SAME

CROSS-REFERENCE TO RELATED APPLICATION

This application claims the benefit of U.S. Provisional Application No. 61/971,435, filed on Mar. 27, 2014, which is hereby incorporated by reference in its entirety.

BACKGROUND

Various types of plastic tubing can include a relatively thin wall with a helical reinforcement. Such corrugated tubing can provide crush resistance while leaving the tubing flexible enough to allow for short-radius bends without collapsing or kinking the tubing. The versatility of this kind of tubing is evidenced by its use in construction, ventilation, manufacturing processes, auto washes, hospitals, medical devices, and other areas.

For certain uses of the above-described tubing, such as for medical uses, it is also desired to provide interior and exterior surfaces mostly free of crevices to eliminate or reduce contaminates that may reside in such crevices. In the case of inhalation therapies such as those using CPAP (Continuous Positive Airway Pressure) and other breathing assistance methods, a smooth inner bore for the tubing is also desired to reduce flow resistance when airflow is conducted through the tubing.

To obtain relatively crevice-free interior and exterior surfaces, the above-described tubing can be manufactured by extruding a plastic strip or ribbon and helically wrapping the ribbon upon itself while molten to form a tubing wall. In such a manufacturing process, a winding or wrapping head with multiple cantilevered and rotationally driven mandrels or winding rolls can be spaced about a longitudinal axis for winding and rotationally advancing helically wound tubing. In some examples, at least one wire and a thermoplastic reinforcement can be placed on the tubing wall while the tubing wall is formed. In such examples, the thermoplastic reinforcement heat bonds to the tubing wall. The tubing is then cooled to solidify before being cut into predetermined lengths.

SUMMARY

Although the helically reinforced plastic tubing described above can provide crush resistance while leaving the tubing wall flexible enough to allow for short-radius bends without collapsing or kinking, portions of such tubing can become easily damaged in the field. In one example, damage may occur to the ends of the tubing due to connections of the tubing to a particular machine such as a CPAP machine. Such damage to the tubing ends may occur, for example, after repeated connection and disconnection of the tubing in the field or from the additional stress on the tubing ends when the tubing is moved while connected. The tubing ends may deform over time due to such mechanical stress or from thermal stress, and in some cases, the connection of the tubing may become compromised.

Although using heavier materials or thickening the tubing wall may provide a more durable tubing, this generally results in a heavier tubing with an increased cost. Heavier tubing can make the tubing more cumbersome to use, such as when the tubing is a vacuum hose that is physically moved by an operator or where a heavier medical device tubing can result in decreased patient comfort and mobility.

In view of the foregoing, the plastic tubing of the present disclosure includes a tubing wall and a helical thermoplastic reinforcement located around and along the tubing wall where at least a thickness of the tubing wall or a size of the reinforcement is varied along the tubing wall. By varying the thickness of the tubing wall and/or the size of the reinforcement, it is ordinarily possible to increase the durability of the tubing at particular locations along the tubing without increasing the weight and cost of the tubing over the entire length of tubing.

For example, by having the ends of the tubing with a thicker wall and/or a larger helical reinforcement, the durability of the tubing is ordinarily improved where the tubing is connected. In addition, a different size for the tubing wall and/or the helical reinforcement at an end of the tubing can allow for a tighter fit to a connection or can allow for connections having a different diameter than other portions of the tubing. For example, one end of the tubing may have a first outer diameter while the other end and/or a middle portion of the tubing may have a different outer diameter.

Furthermore, increasing the size of the tubing wall and/or the helical thermoplastic reinforcement at the end portions can improve cutting of the tubing during manufacturing since the increased size can often provide a cleaner cut than a thinner material which may be more likely to deform or rotate during cutting.

In other implementations, a heavier or thicker tubing may only be needed at certain points between the ends of the tubing or in addition to the ends of the tubing. For example, tubing for a particular machine may only need increased durability at its ends and at a midpoint where the tubing is mounted in the machine.

In one embodiment of the present disclosure, a plastic tubing includes a thermoplastic ribbon helically wrapped and heat bonded to itself to form a tubing wall. The tubing wall along its length includes a first end portion, a second end portion, and a middle portion between the first end portion and the second end portion. The tubing wall is thicker at the first end portion and at the second end portion than throughout the middle portion of the tubing wall, and a helical thermoplastic reinforcement is located around and along the tubing wall.

According to other embodiments, the helical thermoplastic reinforcement is larger at the first and second end portions than throughout the middle portion instead of or in addition to the tubing wall being thicker at the first and second end portions.

In another embodiment, a first cross section of the thermoplastic ribbon across a width of the thermoplastic ribbon has a greater area than a second cross section of the thermoplastic ribbon, with the second cross section located away from the first cross section along a length of the helically wrapped thermoplastic ribbon.

According to another embodiment, a first cross section of the helical thermoplastic reinforcement across a width of the reinforcement has a greater area than a second cross section of the helical thermoplastic reinforcement, with the second cross section located away from the first cross section along a length of the reinforcement.

According to another embodiment, a method of making plastic tubing includes forming a ribbon of molten thermoplastic and helically wrapping the ribbon so that a portion of the ribbon overlaps upon itself and heat bonds to form a tubing wall. A thickness of the ribbon of molten thermoplastic is varied to vary a thickness of the tubing wall.

According to yet another embodiment, a thermoplastic reinforcement is formed and helically disposed around and along the tubing wall to heat bond with the tubing wall with a size of the thermoplastic reinforcement being varied along the tubing wall. In yet another embodiment, both the thickness of the ribbon of molten thermoplastic and the size of the thermoplastic reinforcement are varied.

BRIEF DESCRIPTION OF THE DRAWINGS

The features and advantages of the embodiments of the present disclosure will become more apparent from the detailed description set forth below when taken in conjunction with the drawings. The drawings and the associated descriptions are provided to illustrate embodiments of the disclosure and not to limit the scope of what is claimed.

FIG. 1A is a side view of plastic tubing according to an embodiment.

FIG. 1B depicts a cross section of a tubing wall of the plastic tubing of FIG. 1A according to an embodiment.

FIG. 1C depicts another cross section of the tubing wall of the plastic tubing of FIG. 1A according to an embodiment.

DETAILED DESCRIPTION

Figure 2A:
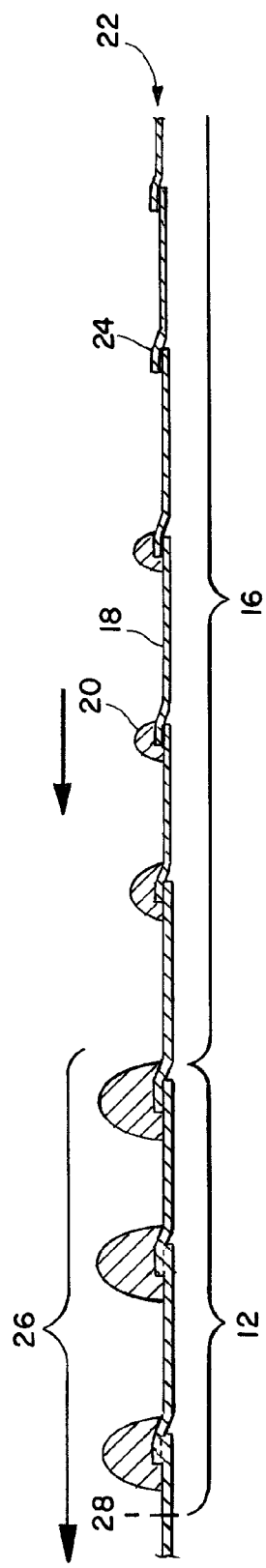
FIG. 2A depicts a lengthwise cross sectional view of a plastic tubing during manufacture including a thickened end portion of a tubing wall with a larger helical thermoplastic reinforcement according to an embodiment.

In the following detailed description, numerous specific details are set forth to provide a full understanding of the present disclosure. It will be apparent, however, to one of ordinary skill in the art that the various embodiments disclosed may be practiced without some of these specific details. In other instances, well-known structures and techniques have not been shown in detail to avoid unnecessarily obscuring the various embodiments.

FIG. 1A is a side view of plastic tubing according to an embodiment where the tubing wall is thicker and the thermoplastic reinforcement is larger at the end portions of the tubing than throughout the middle portion of the tubing. As shown in FIG. 1A, tubing 10 includes first end portion 12, second end portion 14, and middle portion 16, which is located between first end portion 12 and second end portion 14. Tubing 10 includes thermoplastic ribbon 18 which has been helically wrapped and heat bonded to itself to form tubing wall 22.

In addition, tubing 10 includes helical thermoplastic reinforcement 20, which is located around and along tubing wall 22. In the embodiment of FIG. 1A, helical thermoplastic reinforcement 20 is a bead of extruded thermoplastic that has been wrapped around tubing wall 22 and heat bonded with tubing wall 22. As discussed in more detail below with reference to FIGS. 5 and 6, helical reinforcement 20 can be separately extruded from the extrusion of thermoplastic ribbon 18. In other embodiments, helical reinforcement 20 can include a rib or protrusion from ribbon 18 such that helical reinforcement 20 is extruded with ribbon 18. Examples of thermoplastics used for either ribbon 18 or reinforcement 20 can include polyethylene (PE), polypropylene (PP), or any other thermoplastic.

End portions 12 and 14 are not limited to a particular length or proportion of tubing 10. In this regard, end portions 12 and 14 can be several inches in some implementations or can be less than half an inch in other implementations. The length of end portions 12 and 14 can also differ from each other. Similarly, middle portion 16 is not limited to a particular length or proportion of tubing 10.

In FIG. 1A, cross section lines 1B and 1C are provided to show locations for cross sectional views of tubing wall 22 in FIGS. 1B and 1C, respectively. As shown in FIGS. 1B and 1C, tubing wall 22 is thicker for end portions 12 and 14 than throughout middle portion 16. A thickness or outer circumference of tubing wall 22 is shown to be the same at end portions 12 and 14, however, in practice, the thickness of tubing wall 22 may vary slightly such that the thickness of tubing wall 22 will be approximately the same (e.g., within 5% of each other). The thickness of tubing wall 22 may also generally increase in middle portion 16 during the transition from middle portion 16 to either of end portions 12 and 14. However, in the example of FIGS. 1A to 1C, the thickness of tubing wall 22 is generally 15% thicker on average for end portions 12 and 14 than for middle portion 16. This can ordinarily provide a more durable tubing wall at end portions 12 and 14 while allowing for a thinner, more flexible, and lighter tubing wall throughout middle portion 16. Other embodiments can include different changes in thickness of tubing wall 22.

Helical reinforcement 20 is also larger for end portions 12 and 14 than for middle portion 16. In one implementation, reinforcement 20 is on average 20% larger for end portions 12 and 14 than for middle portion 16. As with tubing wall 22, the average increase in size of reinforcement 20 may differ in other embodiments.

Without magnification, tubing 10 may appear in some implementations as though tubing wall 22 and reinforcement 20 have a uniform size across end portions 12 and middle portion 16. This appearance can be due to a relatively small dimensional scale for tubing wall 22 and reinforcement 20. In some implementations, the difference in thickness, height, or width may only be noticeable by measurement with calipers or other fine measurement tools. For example, in an implementation where the thickness of tubing wall 22 increases on average by approximately 14% in end portions 12 and 14 compared to middle portion 16, the measured difference in the average thickness of tubing wall 22 may be 0.03 mm. Similarly, the average height and width of the profile of reinforcement 20 may increase by 9% and 13%, respectively, but with an average increase in height of 0.15 mm and an average increase in width of 0.35 mm. Accordingly, the variation in tubing wall thickness or reinforcement size may be more or less noticeable to the naked eye depending on the dimensional scale of tubing wall 22 and reinforcement 20. In this regard, the variation in tubing wall thickness or reinforcement size will generally be more noticeable where dimensions of tubing wall 22 or reinforcement 20 are larger than the example dimensions provided above.

Although end portions 12 and 14 include a thickened tubing wall 22 and a larger reinforcement 20 than middle portion 16, other embodiments can include one or both of these features at only one of end portion 12 or end portion 14, or in middle portion 16 instead of at the end portions.

FIG. 2A depicts a lengthwise cross sectional view of a plastic tubing which includes an end portion with a thickened tubing wall 22 and a larger helical reinforcement 20 according to an embodiment. As shown in FIG. 2A, ribbon 18 is helically wrapped and heat bonded to itself to form tubing wall 22. Cross sections of ribbon 18 are shown in FIG. 2A across the width of successive wraps of ribbon 18. A portion of each wrap of ribbon 18 overlaps upon a previous wrap of ribbon 18 at overlaps 24, which are shown somewhat exaggerated for ease of explanation. In most implementations, overlaps 24 are virtually coplanar heat bonds.

The last two overlaps on the left side of FIG. 2A are shown with a dashed line rather than a solid line to illustrate the fusing of the wraps of ribbon 18 into an integral whole. The overlaps at what were once individual parts is indicated in FIGS. 2A to 4 with dashed lines.

In addition, helical reinforcement 20 is disposed onto overlaps 24 and heat bonds to form an integral part of tubing 10. In other embodiments, helical reinforcement 20 can be located away from overlaps 24 or on top of another portion of ribbon 18 or on an intermediate layer on tubing wall 22. In yet other embodiments, reinforcement 20 can be a part of ribbon 18 such as a rib or a protrusion from ribbon 18.

The cross sectional view of FIG. 2A provides a view of tubing 10 as it is being formed and before it is cut along cut line 28. Ribbon 18 is initially overlapped on the right side of FIG. 2A forming overlap 24. The amount of overlap of ribbon 18 can vary in different embodiments so that the width of overlap 24 varies from that shown in FIG. 2A. Reinforcement 20 is then disposed on overlap 24 as ribbon 18 and reinforcement 20 are advanced in the direction of the arrow.

As shown in FIG. 2A, the cross sections of ribbon 18 in end portion 12 have a greater area or profile across a width of ribbon 18 than the cross sections of ribbon 18 in middle portion 16. In addition, the cross sections of reinforcement 20 are larger in end portion 12 than in middle portion 16. The durability of the tubing in end portion 12 is generally improved by increasing the size of ribbon 18 and reinforcement 20 while keeping middle portion 16 relatively flexible and lightweight. In other embodiments, a different number of wraps of ribbon 18 and/or reinforcement 20 are possible so as to have a different number of cross sections for ribbon 18 and/or reinforcement 20 than those shown in FIG. 2A.

In the example of FIG. 2A, tubing wall 22 is cut within thickened portion 26, where tubing wall 22 has been thickened and the size of reinforcement 20 has been increased. By cutting tubing wall 22 within thickened portion 26, an end portion for another tubing can be formed to the left of end portion 12. In addition, cutting the tubing within a thickened portion of tubing wall 22 and/or a larger portion of helical thermoplastic reinforcement ordinarily reduces the likelihood of deformation to tubing wall 22 or reinforcement 20 from cutting at cut line 28.

Figure 2B:
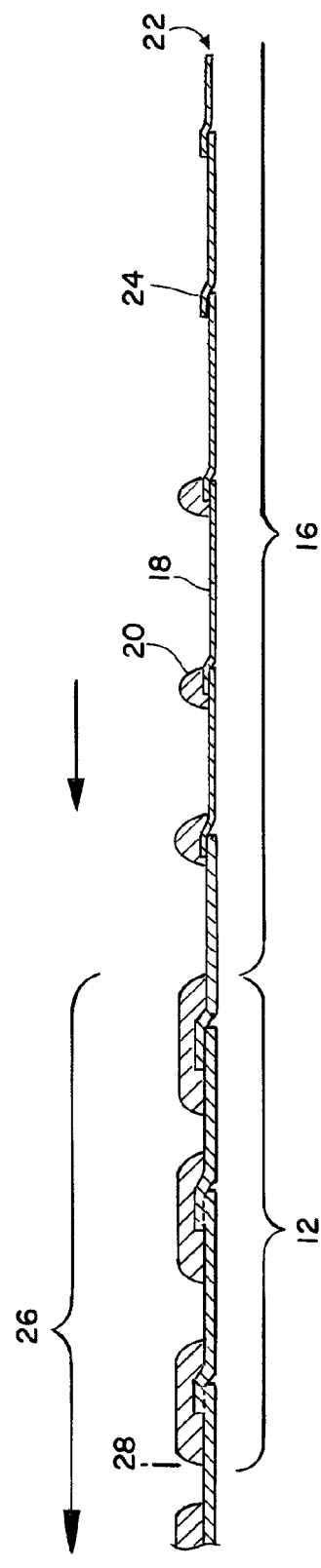
FIG. 2B depicts a lengthwise cross sectional view of a plastic tubing during manufacture with a flattened helical thermoplastic reinforcement along an end portion of a tubing wall according to an embodiment.

FIG. 2B depicts a lengthwise cross sectional view of tubing with a flattened helical reinforcement along end portion 12 of tubing wall 22 according to an embodiment. As with FIG. 2A, the cross sections of reinforcement 20 and ribbon 18 in end portion 12 have more area than the cross sections of reinforcement 20 and ribbon 18 in middle portion 16. However, reinforcement 20 has been flattened in thickened portion 26, which includes end portion 12. Although reinforcement 20 may be taller in middle portion 16, reinforcement 20 is larger with a greater cross sectional area in end portion 12 than in middle portion 16.

Figure 2C:
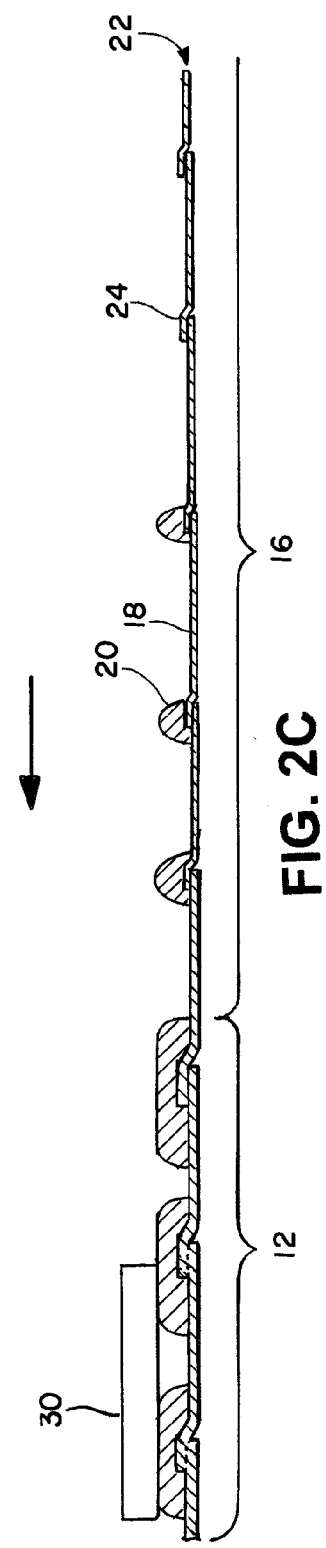
FIG. 2C depicts a lengthwise cross sectional view of a plastic tubing during manufacture with a cuff on an end portion of a tubing wall according to an embodiment.

A roller can be used to flatten reinforcement 20 soon after ribbon 18 has been overlapped to form tubing wall 22 before it completely hardens. Even in a flattened state, increasing the size of reinforcement 20 within end portion 12 ordinarily provides better durability of the tubing. In some implementations, reinforcement 20 is flattened to better accommodate a cuff encircling at least part of end portion 12, as shown in FIG. 2C with cuff 30.

The amount of end portion 12 that is covered by cuff 30 can differ based on different design criteria for the tubing, such as for different amounts of strain relief. For example, some implementations may include several inches of end portion 12 that is not covered by cuff 30 while other implementations may include very little or no portion of end portion 12 that is not covered by cuff 30.

Figure 2D:
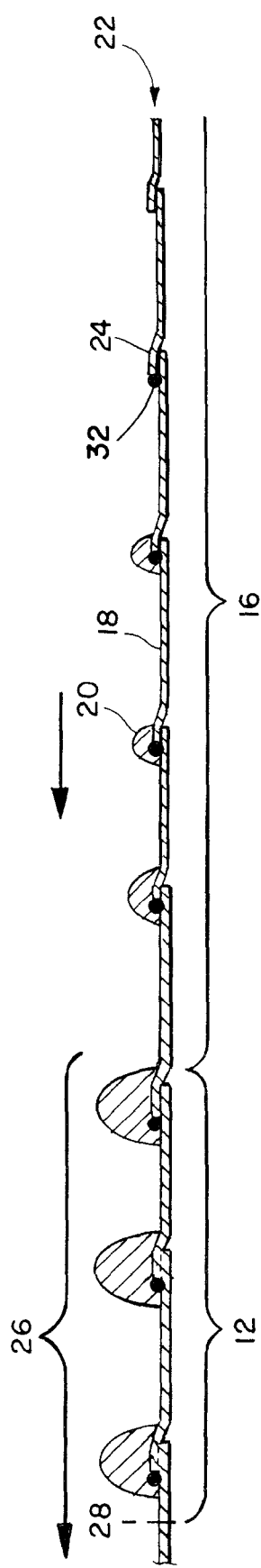
FIG. 2D depicts a lengthwise cross sectional view of a plastic tubing during manufacture including a wire disposed around and along a tubing wall according to an embodiment.

FIG. 2D depicts a lengthwise cross sectional view of plastic tubing including wire 32 disposed around and along tubing wall 22 according to an embodiment. As with the tubing of FIGS. 2A to 2C, the tubing of FIG. 2D includes ribbon 18 and helical reinforcement 20, which are both larger in end portion 12 than in middle portion 16. However, the example of FIG. 2D includes wire 32 helically disposed adjacent overlaps 24. Wire 32 can be wrapped around tubing wall 22 after ribbon 18 has been helically wrapped to form overlap 24. In some implementations, wire 32 can be used to heat a fluid such as air conducted inside tubing wall 22. In other implementations, wire 32 can be used to transmit signals along tubing 10.

For resistance heating purposes, wire 32 can be formed of copper, although resistive metal such as nickel-chromium may also be used. For transmitting signals, wire 32 can include an electrically or optically conductive material such as metals, conductive polymers, or optical fiber. Wire 32 may also include a twisted pair of electrical conductors.

In the embodiment of FIG. 2D, reinforcement 20 is disposed helically on top of wire 32 to insulate wire 32 as well as to provide crush and kinking resistance for tubing 10. In other embodiments, the tubing can include multiple wires positioned adjacent, on or away from overlaps 24.

Figure 2E:
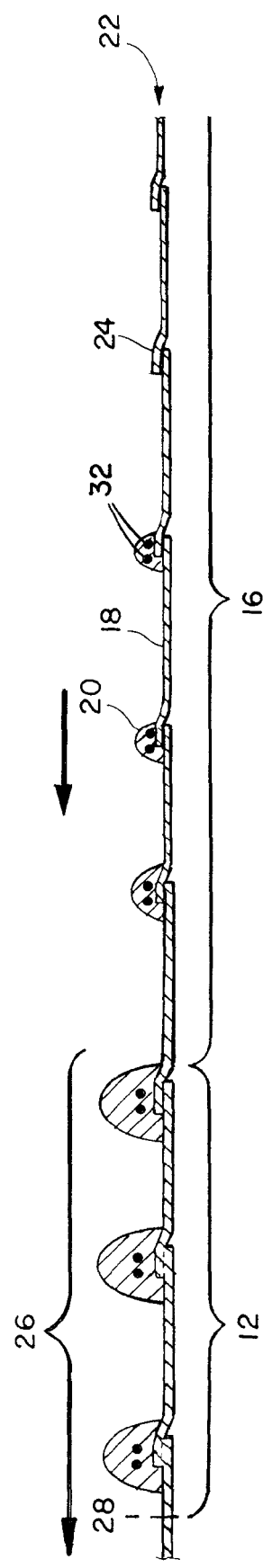
FIG. 2E depicts a lengthwise cross sectional view of a plastic tubing during manufacture including wires within a helical thermoplastic reinforcement according to an embodiment.

FIG. 2E depicts a lengthwise cross sectional view of an embodiment of a plastic tubing including multiple wires 32 within helical reinforcement 20. In such an embodiment, wires 32 can be embedded within reinforcement 20 before reinforcement 20 is helically disposed on tubing wall 22. Wires 32 in FIG. 2E can be used for heating and/or electric signal transmission along the tubing.

As with the tubing of FIGS. 2A to 2D, both the cross sections of ribbon 18 and reinforcement 20 are larger in end portion 12 than in middle portion 16.

Figure 2F:
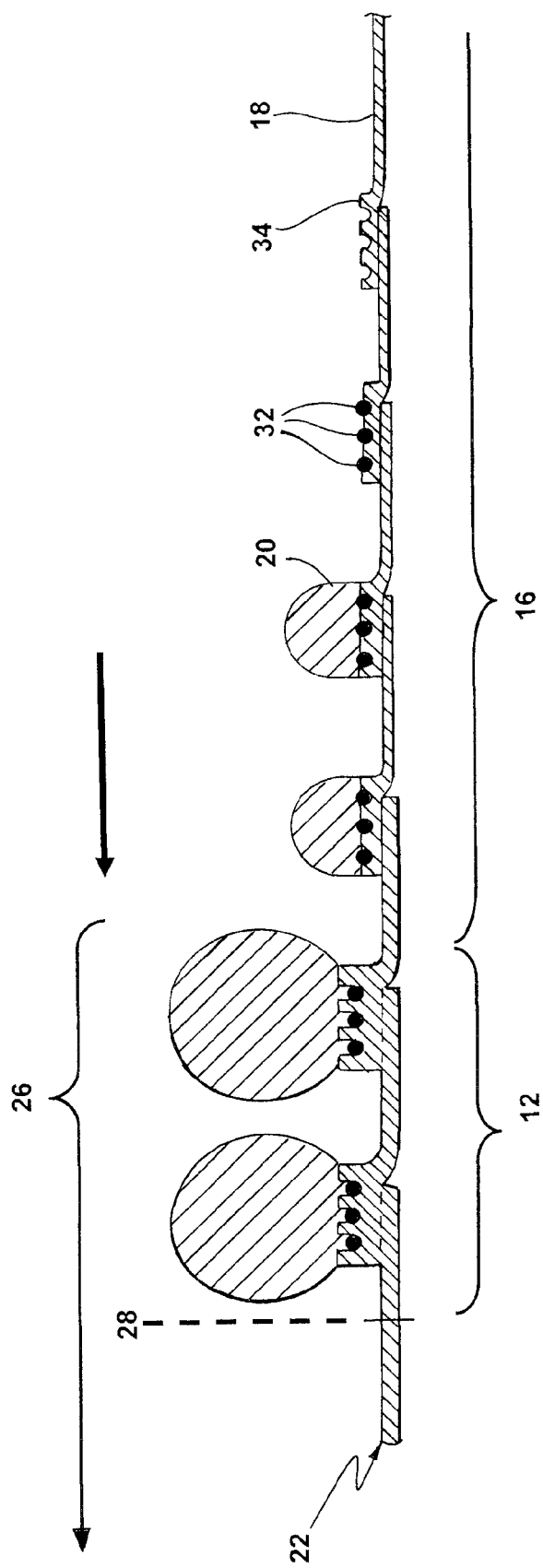
FIG. 2F depicts a lengthwise cross sectional view of a plastic tubing during manufacture including a grooved plateau according to an embodiment.

FIG. 2F depicts a lengthwise cross sectional view of an embodiment of a plastic tubing including grooved plateau 34 on one end of ribbon 18. Plateau 34 is elevated along an edge of ribbon 18 so as to helically wrap around and along tubing wall 22. As shown in FIG. 2F, three wires 32 are placed in grooves of plateau 34 before reinforcement 20 is placed upon plateau 34 to cover wires 32. The location of plateau 34 is not limited to a particular location. In addition, the number or arrangement of wires 32 may differ in other embodiments.

As with the tubing of FIGS. 2A to 2E, both the cross sections of ribbon 18 and reinforcement 20 are larger in end portion 12 than in middle portion 16. Although the thickness of ribbon 18 may vary across a width of ribbon 18 due to plateau 34, the area of each cross section of ribbon 18 across its width (including plateau 34) is greater in end portion 12 than the areas of each cross section of ribbon 18 in middle portion 16.

Figure 3:
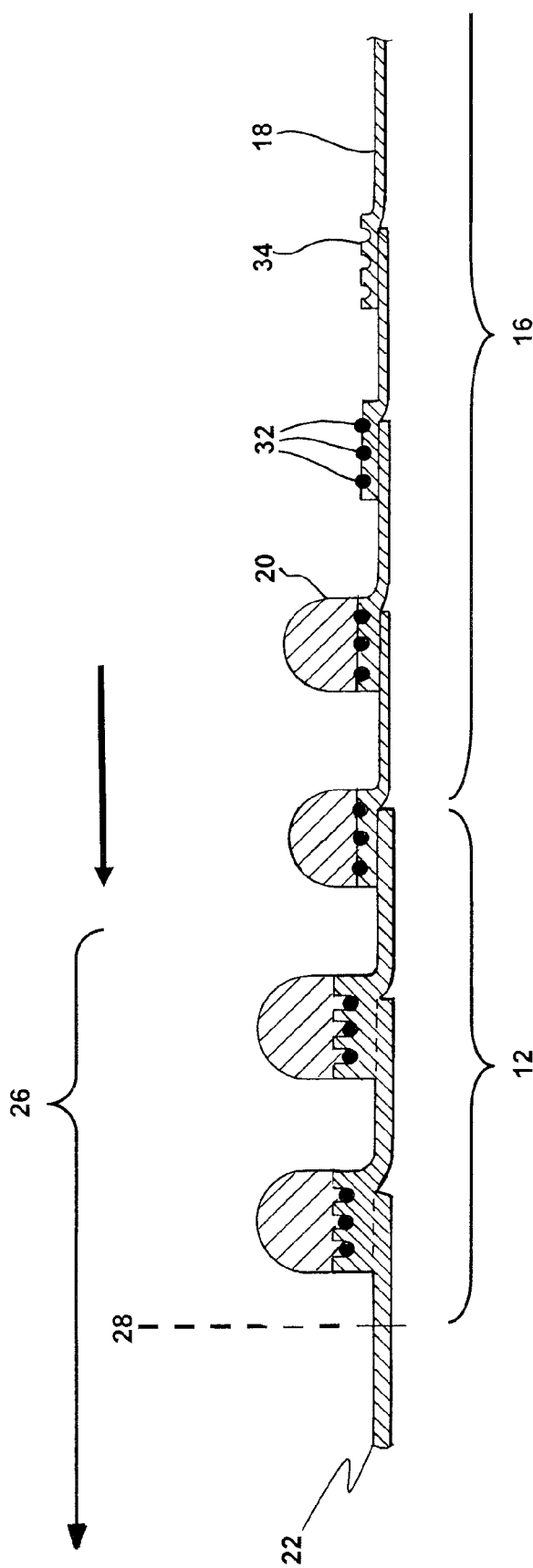
FIG. 3 depicts a lengthwise cross sectional view of a plastic tubing during manufacture including a thickened tubing wall according to an embodiment.

FIG. 3 depicts a lengthwise cross sectional view of a plastic tubing according to an embodiment where tubing wall 22 is thicker in end portion 12, but reinforcement 20 remains substantially the same size as in middle portion 16. As shown in FIG. 3, each cross section of ribbon 18 in end portion 12 has a greater area across a width of ribbon 18 than the cross sections of ribbon 18 in middle portion 16.

Figure 4:
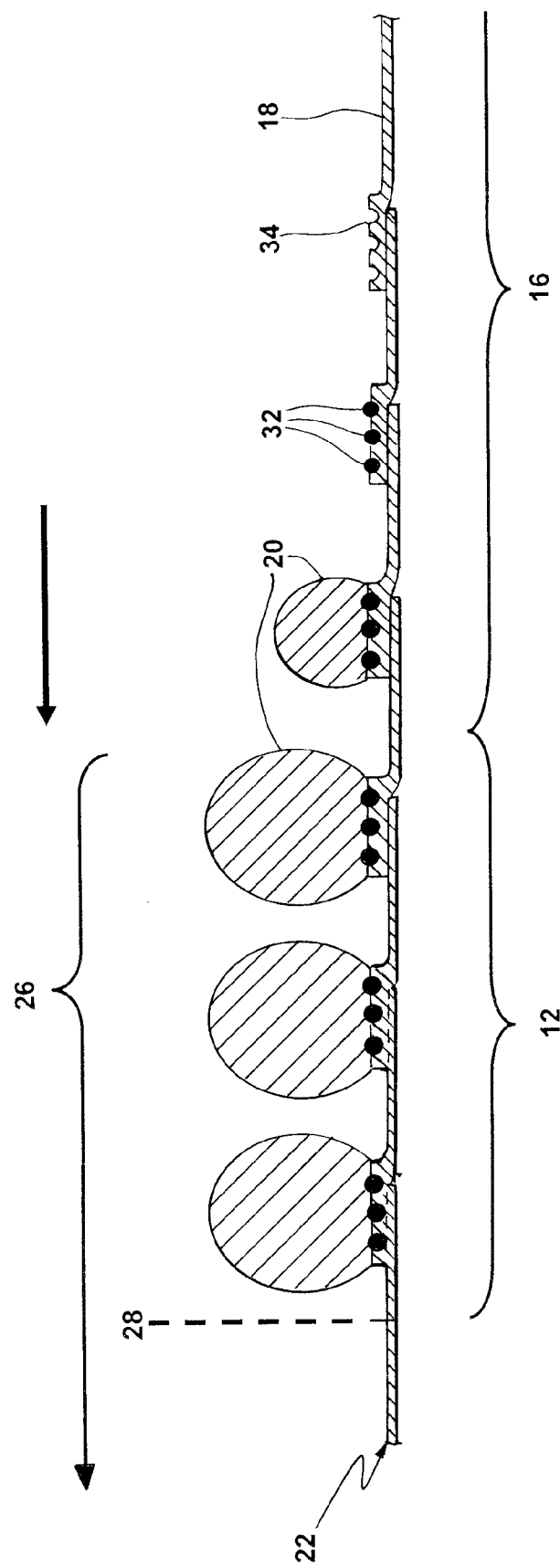
FIG. 4 depicts a lengthwise cross sectional view of a plastic tubing during manufacture including a helical thermoplastic reinforcement that has been increased in size according to an embodiment.

FIG. 4 depicts a lengthwise cross sectional view of an embodiment where reinforcement 20 has been increased in size in end portion 12, but ribbon 18 remains substantially the same size in both middle portion 16 and end portion 12. As shown in FIG. 4, each cross section of reinforcement 20 in end portion 12 has a greater area across the width of reinforcement 20 than the cross sections of reinforcement 20 in middle portion 16. Such an increase in the size of reinforcement 20 can allow for increased durability of the tubing while not significantly interfering with thermal conduction from wires 32 to fluid conducted within the tubing. The example of FIG. 4 may also allow for flexibility of tubing wall 22 in end portion 12 by not also thickening tubing wall 22.

Figure 5:
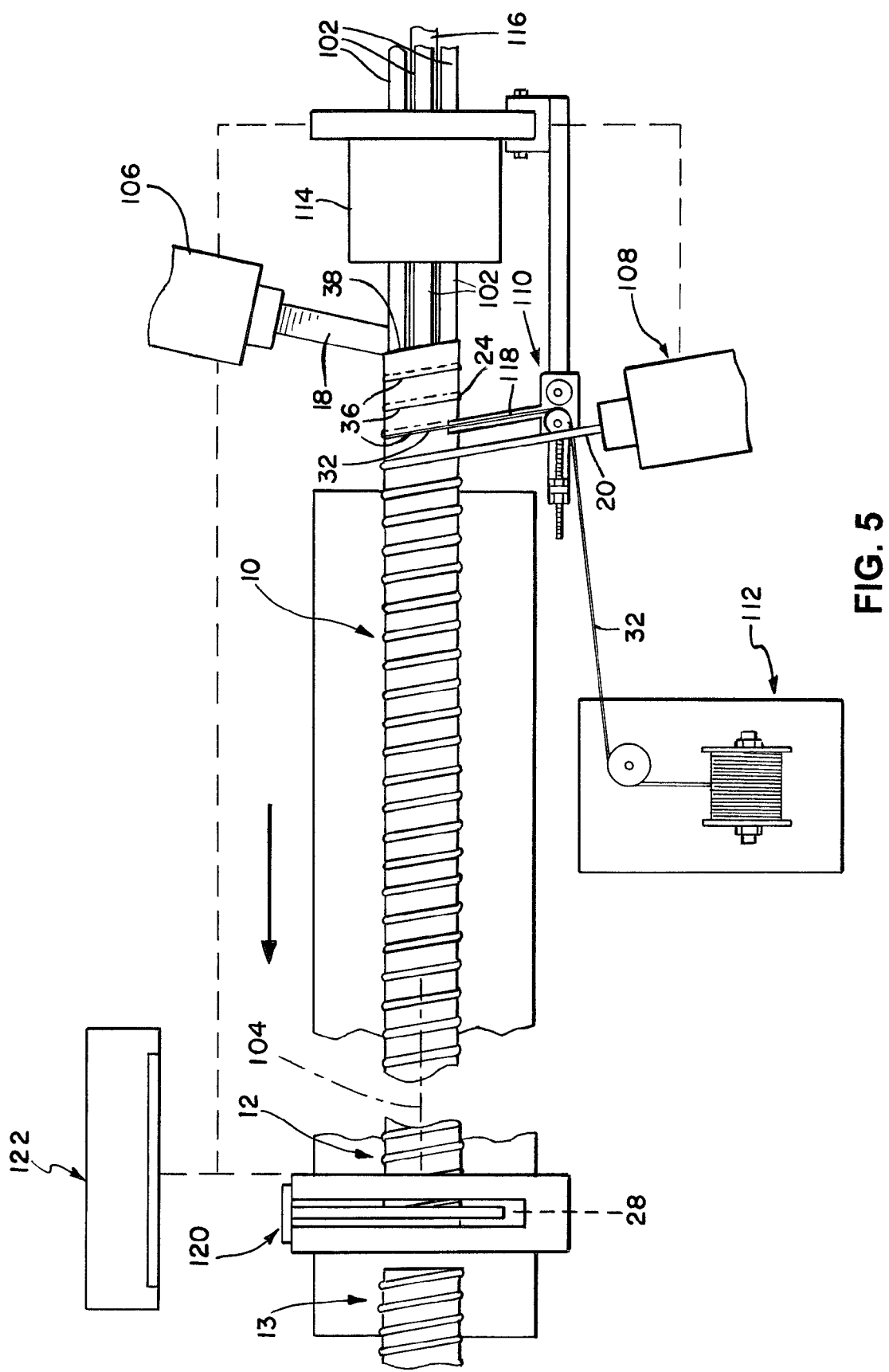
FIG. 5 is a top view of a layout for manufacturing plastic tubing according to an embodiment.

FIG. 5 is a top view of a layout for manufacturing plastic tubing 10 according to an embodiment. As shown in FIG. 5, mandrel motor 114 is configured to rotate mandrels 102, which are canted and spaced about longitudinal axis 104 for winding and rotationally advancing tubing 10. In one implementation, the mandrels can rotate together in a clockwise direction.

First extruder 106 is configured to extrude ribbon 18 including leading edge 36 and trailing edge 38. Second extruder 108 is configured to extrude thermoplastic reinforcement 20. Although first extruder 106 and second extruder 108 are shown as physically separate extruding machines for ease of explanation in FIG. 5, it should be understood that both ribbon 18 and reinforcement 20 may be extruded from a single extrusion machine with a co-located die.

Ribbon 18 is discharged in a molten state from first extruder 106 and helically wrapped about mandrels 102 so that it encircles mandrels 102 and wraps upon itself at overlap 24 to form successive wraps of ribbon 18 in tubing wall 22. As tubing wall 22 cools and solidifies, it is advanced toward the left in the direction of the arrow Wire feeding mechanism 110 employs payout mechanism 112 for feeding and embedding wire 32 along leading edge 36 of each overlap 24 just prior to application of reinforcement 20 to tubing 10 as shown. Wire 32 is fed at a particular draw angle using trough 118 as a guide.

The canting of mandrels 102 causes tubing 10 to move continuously in a downstream direction indicated by the arrow. In the example embodiment of FIG. 5, cooling conduit 116 sprays water directed radially outwardly against the inner surface of tubing 10, and also in the downstream direction which assists in removing tubing 10 after cutting.

Cutting mechanism 120 is configured to cut tubing 10 in determined lengths. In the embodiment of FIG. 5, cutting mechanism 120 is configured to periodically cut tubing 10 at a predetermined time period corresponding to a particular length for tubing 10. In addition, the cutting of tubing 10 is coordinated with mandrel motor 114 so as to occur at cut line 28 to form end portions 12 and 13, which include a thickened tubing wall 22 and/or a larger reinforcement 20. In this regard, the cutting of tubing 10 can also be coordinated with a speed of extruder 106, extruder 108, and/or mandrel motor 114. As described in more detail below with reference to FIG. 6, increasing the speeds of extrusion of ribbon 18 and reinforcement 20 with respect to the speed of mandrel motor 114 can result in a thickening of tubing wall 22 and a larger reinforcement 20. In addition, the slowing of mandrel motor 114 with respect to the speeds of extruders 106 and 108 can result in a thickening of tubing wall 22 and a larger reinforcement 20.

As shown in FIG. 5, the coordination of cutting mechanism 120 with extruder 106, extruder 108, and/or mandrel motor 114 can be accomplished through programming at controller 122, which is electrically connected to extruder 106, mandrel motor 114, and extruder 108. Controller 122 can include a processor for executing computer-readable instructions stored in a memory of controller 122. In addition, controller 122 can include a user interface such as a touchscreen to allow for configuration of the operation of cutting mechanism 120, mandrel motor 114, and extruders 106 and 108. In other embodiments, the configuration of operation for any of cutting mechanism 120, mandrel motor 114, and extruders 106 and 108 can be accomplished by separate controllers for each of these devices.

Figure 6:
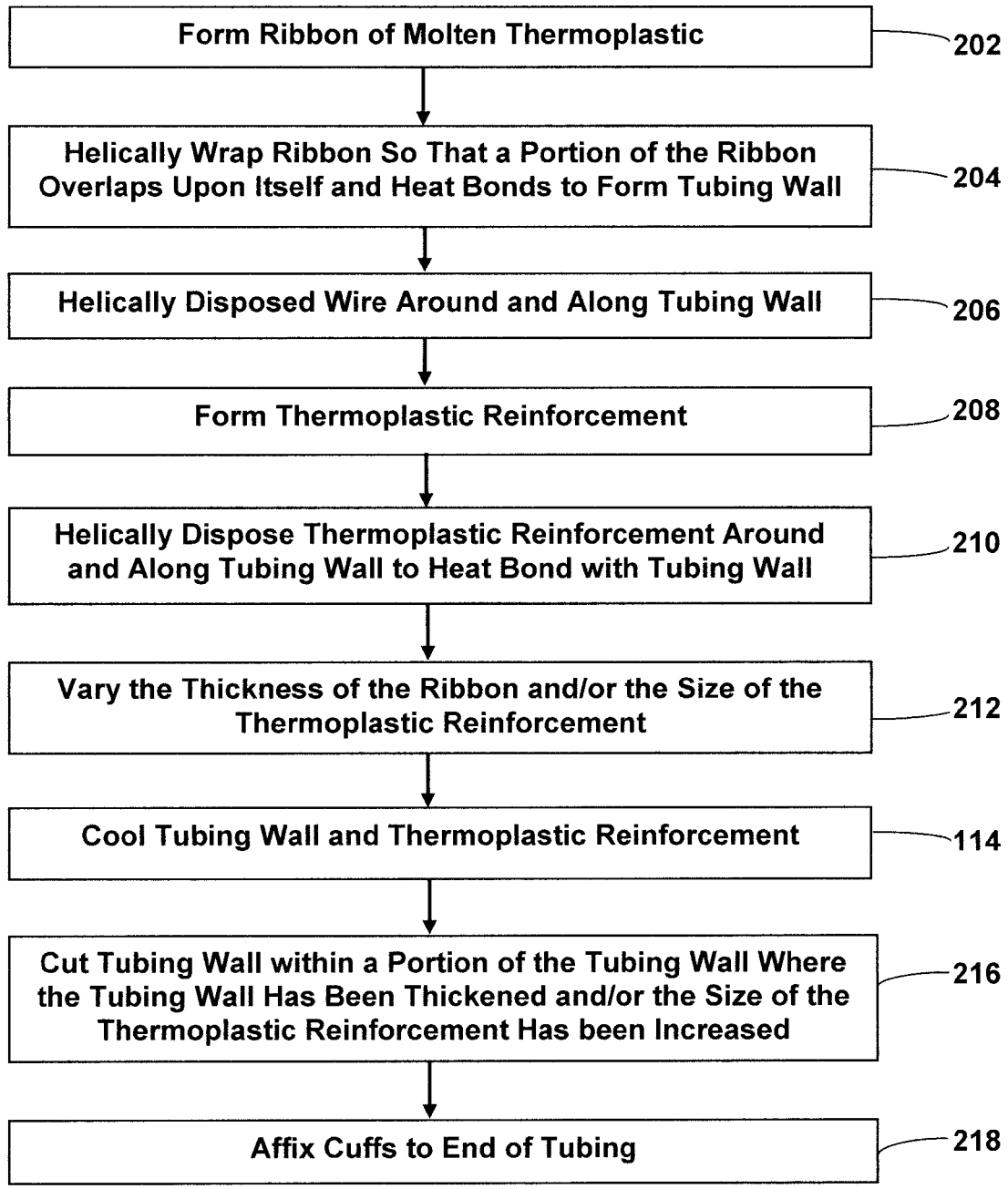
FIG. 6 is a flowchart for a plastic tubing manufacturing process according to an embodiment.

FIG. 6 is a flowchart for a plastic tubing manufacturing process according to an embodiment. The process of FIG. 6 begins with forming ribbon 18 of molten thermoplastic in block 202. This can be accomplished using an extruder such as extruder 106 in FIG. 5. Ribbon 18 is then helically wrapped around rotating mandrels 102 in block 204 so that a portion of ribbon 18 overlaps upon itself and heat bonds to form tubing wall 22.

In block 206, wire 32 is helically disposed around and along tubing wall 22 using wire feeding mechanism 110, payout mechanism 112, and trough 118 to guide wire 32 onto leading edge 36 at a particular draw angle. In other embodiments, multiple wires may be helically disposed around and along tubing wall 22 or wire 32 may be located on a different portion of tubing wall than leading edge 36, such as into a groove along tubing wall 22. In yet other embodiments, block 206 may be omitted so that no wires are helically disposed on tubing wall 22.

In block 208, thermoplastic reinforcement 20 is formed by extruder 108. Reinforcement 20 can also be molten when formed as with ribbon 18 or may have already cooled so that it is no longer molten. Conversely, ribbon 18 may have already been cooled and thermoplastic reinforcement 20 can be molten. In other embodiments, reinforcement 20 and ribbon 18 can be formed together so that ribbon 18 and reinforcement 20 are formed by the same extruder. In such an embodiment, reinforcement 20 can include a rib or other protrusion extending from ribbon 18.

In block 210, reinforcement 20 is helically disposed around and along tubing wall 22 to heat bond with tubing wall 22. As shown in FIG. 5, reinforcement 20 is disposed so as to cover or encircle wire 32 at overlap 24. In other embodiments, reinforcement 20 can be disposed at other locations around and along tubing wall 22 such as between overlaps 24. In some embodiments, a roller may also flatten a portion of reinforcement 20 soon after reinforcement 20 is located on tubing wall 22 as shown in the tubing of FIGS. 2B and 2C.

In block 212, either the thickness of ribbon 18 or the size of reinforcement 20 is varied, or both the thickness of ribbon 18 and the size of reinforcement 20 are varied. In one implementation, varying the thickness of ribbon 18 includes varying a speed at which extruder 106 extrudes ribbon 18 while mandrel motor 114 is kept at the same speed. When extruder 106 is sped up, ribbon 18 becomes thicker since tubing wall 22 continues to advance at the same rate. Extruder 106 can be configured to speed up for a certain period of time for thickened end portions of tubing wall 22, and then return to the slower speed for a thinner middle portion 16 of tubing wall 22. Extruder 106 can alternate between the two different speeds. In one example, a motor of extruder 106 may speed up to a high RPM for two seconds, slow down to a low RPM for six seconds, and then speed back up to the high RPM for two seconds This cycle can be repeated so as to form successive end portions and middle portions.

Extruder 108 can also be sped up in block 212 while mandrel motor 114 remains at the same speed to form a larger reinforcement 20. Similar to extruder 106, extruder 108 can be configured to speed up for certain period of time for a larger reinforcement 20 along end portions of tubing wall 22, and then return to the slower speed for a smaller reinforcement 20 along middle portion 16 of tubing wall 22.

In other embodiments, a speed of mandrel motor 114 can be varied with respect to the speed of either or both extruders 106 and 108 to vary either or both the thickness of tubing wall 22 and the size of reinforcement 20. If mandrel motor 114 is slowed down while extruders 106 and 108 remain at the same speeds, tubing wall 22 becomes thicker and reinforcement 20 increases in size. In another example implementation, if mandrel motor 114 and extruder 106 are slowed down while extruder 108 remains at the same speed, reinforcement 20 increases in size while tubing wall 22 remains substantially the same size. To increase a thickness of tubing wall 22, mandrel motor 114 and extruder 108 can be slowed down while extruder 106 remains at the same speed.

In block 214, tubing wall 22 and reinforcement 20 are cooled either by air, water or a combination of both. In the example of FIG. 5, tubing wall 22 and reinforcement 20 can be cooled by both a water bath before reaching cutting mechanism 120 and by cooling from cooling conduit 116. As tubing wall 22 and reinforcement 20 cool, they bond together to form integral components of tubing 10.

In block 216, tubing wall 22 is cut by cutting mechanism 120 within a portion of tubing wall 22 where it has been thickened and/or the size of reinforcement 20 has been increased. Such a portion of tubing wall can correspond to thickened portion 26 so as to form two end portions with a thickened tubing wall and/or a larger reinforcement 20. Cutting mechanism may periodically cut tubing wall 22 so as to repeatedly produce tubing of a determined length as it is advanced along mandrels 102.

In block 218, one or more cuffs such as cuff 30 are affixed to the ends of tubing 10. The cuffs may be affixed via over-molding, or by using other methods known in the art. In other embodiments, block 218 may be omitted such that no cuffs are affixed to the ends of the tubing.

The foregoing description of the disclosed example embodiments is provided to enable any person of ordinary skill in the art to make or use the embodiments in the present disclosure. Various modifications to these examples will be readily apparent to those of ordinary skill in the art, and the principles disclosed herein may be applied to other examples without departing from the spirit or scope of the present disclosure. The described embodiments are to be considered in all respects only as illustrative and not restrictive and the scope of the disclosure is, therefore, indicated by the following claims rather than by the foregoing description. All changes which come within the meaning and range of equivalency of the claims are to be embraced within their scope.

What is claimed is:

1. A plastic tubing, comprising:
   a thermoplastic ribbon helically wrapped and heat bonded to itself to form a tubing wall, wherein a first cross section of the thermoplastic ribbon across a width of the thermoplastic ribbon at a first end portion of the tubing wall has a greater area than a second cross section of the thermoplastic ribbon across the width of the thermoplastic ribbon, the second cross section of the thermoplastic ribbon located away from the first cross section of the thermoplastic ribbon along a length of the helically wrapped thermoplastic ribbon, and wherein a third cross section of the thermoplastic ribbon across the width of the thermoplastic ribbon at a second end portion of the tubing wall has approximately the same area as the first cross section of the thermoplastic ribbon, and wherein the second cross section of the thermoplastic ribbon is located between the third cross section of the thermoplastic ribbon and the first cross section of the thermoplastic ribbon along a length of the helically wrapped thermoplastic ribbon; and
   a helical thermoplastic reinforcement located around and along the tubing wall.

2. The plastic tubing of claim 1, wherein a first cross section of the helical thermoplastic reinforcement across a width of the helical thermoplastic reinforcement has a greater area than a second cross section of the helical thermoplastic reinforcement across the width of the helical thermoplastic reinforcement, the second cross section of the helical thermoplastic reinforcement located away from the first cross section of the helical thermoplastic reinforcement along a length of the helical thermoplastic reinforcement.

3. The plastic tubing of claim 2, wherein a third cross section of the helical thermoplastic reinforcement across the width of the helical thermoplastic reinforcement has approximately the same area as the first cross section of the helical thermoplastic reinforcement, and
   wherein the second cross section of the helical thermoplastic reinforcement is located between the third cross section of the helical thermoplastic reinforcement and the first cross section of the helical thermoplastic reinforcement along a length of the helical thermoplastic reinforcement.

4. The plastic tubing of claim 1, wherein the tubing wall along its length includes a middle portion between the first end portion and the second end portion, and
   wherein the tubing wall is thicker at the first end portion and at the second end portion than throughout the middle portion.

5. The plastic tubing of claim 1, wherein the tubing wall along its length includes a middle portion between the first end portion and the second end portion, and wherein the helical thermoplastic reinforcement is larger at the first end portion and at the second end portion than throughout the middle portion.

6. A plastic tubing, comprising:
a thermoplastic ribbon helically wrapped and heat bonded to itself to form a tubing wall; and
a helical thermoplastic reinforcement located around and along the tubing wall, wherein a first cross section of the helical thermoplastic reinforcement across a width of the helical thermoplastic reinforcement at a first end portion of the tubing wall has a greater area than a second cross section of the helical thermoplastic reinforcement across the width of the helical thermoplastic reinforcement, the second cross section of the helical thermoplastic reinforcement located away from the first cross section of the helical thermoplastic reinforcement along a length of the helical thermoplastic reinforcement, wherein a third cross section of the helical thermoplastic reinforcement across the width of the helical thermoplastic reinforcement at the second end portion of the tubing wall has approximately the same area as the first cross section of the helical thermoplastic reinforcement, and wherein the second cross section of the helical thermoplastic reinforcement is located between the third cross section of the helical thermoplastic reinforcement and the first cross section of the helical thermoplastic reinforcement along the length of the helical thermoplastic reinforcement.

7. The plastic tubing of claim 6, wherein a first cross section of the thermoplastic ribbon across a width of the thermoplastic ribbon has a greater area than a second cross section of the thermoplastic ribbon across the width of the thermoplastic ribbon, the second cross section of the thermoplastic ribbon located away from the first cross section of the helical thermoplastic reinforcement along a length of the helically wrapped thermoplastic ribbon,
wherein a third cross section of the thermoplastic ribbon across the width of the thermoplastic ribbon has approximately the same area as the first cross section of the thermoplastic ribbon, and
wherein the second cross section of the thermoplastic ribbon is located between the third cross section of the thermoplastic ribbon and the first cross section of the thermoplastic ribbon along the length of the helically wrapped thermoplastic ribbon.

8. The plastic tubing of claim 6, wherein the tubing wall along its length includes a middle portion between the first end portion and the second end portion, and
wherein the tubing wall is thicker at the first end portion and at the second end portion than throughout the middle portion.

9. The plastic tubing of claim 6, wherein the tubing wall along its length includes a middle portion between the first end portion and the second end portion, and
wherein the helical thermoplastic reinforcement is larger at the first end portion and at the second end portion than throughout the middle portion.

10. A plastic tubing, comprising:
a thermoplastic ribbon helically wrapped and heat bonded to itself to form a tubing wall, the tubing wall along its length including a first end portion, a second end portion, and a middle portion between the first end portion and the second end portion, wherein a first cross section of the thermoplastic ribbon across a width of the thermoplastic ribbon at the first end portion has a greater area than a second cross section of the thermoplastic ribbon at the middle portion, and wherein a third cross section of the thermoplastic ribbon across a width of the thermoplastic ribbon at the second end portion has a greater area than the second cross section; and
a helical thermoplastic reinforcement located around and along the tubing wall.

11. The plastic tubing of claim 10, wherein the helical thermoplastic reinforcement is larger at the first end portion and at the second end portion of the tubing wall than throughout the middle portion of the tubing wall.

12. The plastic tubing of claim 10, wherein the tubing wall is thicker at the first end portion and at the second end portion than throughout the middle portion.

13. A plastic tubing, comprising:
a thermoplastic ribbon helically wrapped and heat bonded to itself to form a tubing wall, the tubing wall along its length including a first end portion, a second end portion, and a middle portion between the first end portion and the second end portion; and
a helical thermoplastic reinforcement located around and along the tubing wall, wherein a first cross section of the helical thermoplastic reinforcement across a width of the helical thermoplastic reinforcement at the first end portion has a greater area than a second cross section of the helical thermoplastic reinforcement at the second end portion, and wherein a third cross section of the helical thermoplastic reinforcement across a width of the helical thermoplastic reinforcement at the second end portion has a greater area than the second cross section of the helical thermoplastic reinforcement.

14. The plastic tubing of claim 13, wherein the helical thermoplastic reinforcement is larger at the first end portion and at the second end portion of the tubing wall than throughout the middle portion of the tubing wall.

* * * * *